United States Patent
Brehm et al.

(10) Patent No.: US 10,449,282 B2
(45) Date of Patent: Oct. 22, 2019

(54) CONTAINER WITH A CONNECTOR FOR CONNECTION TO A FLUID PREPARATION DEVICE

(71) Applicant: Fresenius Medical Care Deutschland GmbH, Bad Homburg (DE)

(72) Inventors: Winfried Brehm, Hofheim (DE); Philippe Laffay, Sainte Foy les Lyons (FR); Benoit Luaire, Sourcieux les Mines (FR)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 560 days.

(21) Appl. No.: 15/106,628

(22) PCT Filed: Dec. 16, 2014

(86) PCT No.: PCT/EP2014/003373
§ 371 (c)(1),
(2) Date: Jun. 20, 2016

(87) PCT Pub. No.: WO2015/090563
PCT Pub. Date: Jun. 25, 2015

(65) Prior Publication Data
US 2017/0021078 A1    Jan. 26, 2017

(30) Foreign Application Priority Data
Dec. 20, 2013   (EP) .................................... 13005984

(51) Int. Cl.
*A61M 1/16* (2006.01)
*B01F 15/02* (2006.01)
*B01F 15/00* (2006.01)

(52) U.S. Cl.
CPC .......... *A61M 1/1668* (2014.02); *A61M 1/167* (2014.02); *A61M 1/1656* (2013.01);
(Continued)

(58) Field of Classification Search
CPC .. A61M 1/1668; A61M 1/167; A61M 1/1656; A61M 1/1666; A61M 2209/08;
(Continued)

(56) References Cited

U.S. PATENT DOCUMENTS 5,038,951 A * 8/1991 Rizzardi .............. B65D 51/285
                                                206/222
5,540,265 A * 7/1996 Polaschegg ......... A61M 1/1656
                                                141/114
(Continued)

FOREIGN PATENT DOCUMENTS

DE    102011106248    1/2013
EP         0458041    11/1991
(Continued)

*Primary Examiner* — Charles Cooley
(74) *Attorney, Agent, or Firm* — Jacobson, Holman, PLLC.

(57) ABSTRACT

A combination includes a container having a connecting portion, and a fluid preparation device, in particular a dialysis machine. The fluid preparation device is configured for mounting and connecting the connecting portion of the container. The fluid preparation device includes at least one line in fluid communication with an interior of the container in the connected position of the container. The container is filled with a first medium, and includes a reservoir containing a second medium. The fluid preparation device includes a rod-shaped element for opening the reservoir so that the first medium and the second medium are mixed with each other.

10 Claims, 8 Drawing Sheets

(52) U.S. Cl.
CPC ....... *A61M 1/1666* (2014.02); *B01F 15/0087* (2013.01); *B01F 15/0205* (2013.01); *B01F 15/0215* (2013.01); *A61M 2209/08* (2013.01)

(58) Field of Classification Search
CPC .............. B01F 15/0087; B01F 15/0215; B01F 15/0205; B01F 15/0206
See application file for complete search history.

(56) References Cited

U.S. PATENT DOCUMENTS

| | | | | |
|---|---|---|---|---|
| 7,223,262 B2* | 5/2007 | Brehm | ................ | A61M 1/1656 285/124.1 |
| 7,828,788 B2* | 11/2010 | Brehm | ................ | A61M 1/1656 383/210.1 |
| 8,617,134 B2* | 12/2013 | Brehm | ................ | A61M 1/1656 285/124.1 |
| 8,678,224 B2* | 3/2014 | Dumont D'Ayot | ................ | A61M 1/1656 220/500 |
| 9,527,627 B2* | 12/2016 | Eyrard | ................ | A61M 1/1656 |
| 10,022,297 B2* | 7/2018 | Kloeffel | ................ | A61J 1/10 |
| 10,022,299 B2* | 7/2018 | Eyrard | ................ | A61J 1/1406 |
| 10,076,599 B2* | 9/2018 | Eyrard | ................ | A61M 1/1656 |
| 2003/0168120 A1* | 9/2003 | Brehm | ................ | A61M 1/1656 141/313 |
| 2009/0139951 A1* | 6/2009 | Chen | ................ | B65D 51/2835 215/227 |
| 2012/0067898 A1* | 3/2012 | Dumont D'Ayot | ................ | A61M 1/1656 220/500 |
| 2014/0034657 A1* | 2/2014 | Eyrard | ................ | A61M 1/1656 220/601 |
| 2014/0144794 A1* | 5/2014 | Eyrard | ................ | A61J 1/1406 206/219 |
| 2017/0007541 A1* | 1/2017 | Eyrard | ................ | A61K 31/194 |
| 2017/0021078 A1* | 1/2017 | Brehm | ................ | A61M 1/1656 |

FOREIGN PATENT DOCUMENTS

| | | |
|---|---|---|
| WO | WO 2007/144427 | 12/2007 |
| WO | WO 2012/104405 | 8/2012 |
| WO | WO 2013/020989 | 2/2013 |

* cited by examiner

CONTAINER WITH A CONNECTOR FOR CONNECTION TO A FLUID PREPARATION DEVICE

BACKGROUND OF THE INVENTION

1. Field of the Invention

The present invention relates to a combination of a container comprising a connecting portion and of a fluid preparation device, in particular a dialysis machine, which fluid preparation device is suitable for mounting and connecting the connecting portion of the container, wherein the fluid preparation device comprises at least one line which is in fluid communication with the interior of the container at least in the connected position of the container, the container being filled with a first medium

2. Description of Related Art

A combination according to the preamble portion of claim is known from EP 1 344 550 B1. The combination of this document comprises a container which is provided with a connection portion. The connection portion is connected with a mounting connector part of the fluid preparation device. The fluid preparation device comprises a flushing fluid line for providing a fluid such as water into the interior of the container as well as a prepared fluid line for feeding the prepared fluid out of the container to the place of use.

FIG. 7 of the instant application shows a part 50 of a dialysis machine comprising a mounting connector part 58 which is adapted to a mount and connect the connecting portion 32 of the container 30. The mounting connector part 58 comprises a fresh or flushing fluid line 51 for feeding fresh fluid such as water into the interior of the container 30. Reference numeral 52 designates a prepared fluid line for draining the prepared solution such as a dialysis solution out of the container 30. The mounting connector part 58 comprises first 58a and second 58b mounting means which are adapted mate with first 34a and second mounting means 34b of the connecting portion 32 of the container 30.

In the connected state the mounting means 58a, 58b are in fluid communication with the mounting means 34a, 34b respectively so that fresh fluid is flowing through line 51 into the space formed by the mating mounting means 58a and 34a of the connecting portion 32a of the container 30 and from this space into the container.

The container 30 may be filled with a solid or liquid concentrate which is solved or diluted by the fresh fluid.

The solution is drained from the interior of the container into the space formed by the mating mounting means 58b and 34b and from this space into the prepared fluid line 52 for further use (after dilution) such as in a dialysis machine.

Reference numeral 59 designates a switch which is adapted to be depressed when the connecting portion 32 of the container 30 is in place within the mounting connector part 58.

Reference numeral 60 designates a lid which is turnable around a joint 60' from a first open position, which is shown in FIGS. 1 and 7, to one or more closed or locked positions. The lid 60 has first and second closure parts 61a and 61b, which are adapted to close the spaces 58a and 58b when no container 30, i.e., no connecting portion 32, is present in the mounting connector part 58.

Prior art document DE 10 2011 106 248 A1 refers to a combination of a container comprising a connecting portion and of a fluid preparation device, wherein the flushing fluid line and the prepared fluid line are provided by one and the same line. In this case fresh water is supplied through line 52 shown in FIG. 7 and through a space defined by the mounting means 34b and 58b as well as tube which is located within the container. The prepared solution is drained from the container by the same way, i.e. via said tube and the mounting means 34b and 58b and line 52.

It is further known from the prior art to provide a container with a reservoir containing a second medium which is different from the first medium which is present in the container. Reference is made to WO 2013/020989 A1. FIG. 7 shows the connecting portion of a container including such a reservoir 100.

As shown in FIG. 7 the reservoir 100 contains a housing 102 as well as a piston 104 which is moveable relative to the housing. Upon movement of the piston the lower portion of the housing is opened so that the second medium which is contained in the reservoir is mixed with the first medium which is contained in the container.

In case that the step of opening of the reservoir is omitted or not performed correctly the composition of the final solution, such as a dialysis solution or of a concentrate on the basis of which a dialysis solution is produced is not correct.

Apart from this, opening of the reservoir requires interaction of the personal so that the object underlying the present invention is to simplify the handling and furthermore to increase the reliability regarding the correct preparation of the concentrate or solution.

SUMMARY OF THE INVENTION

This object is solved by means of a combination according to the invention described herein.

According to the instant invention, a reservoir containing a second medium is provided wherein the fluid preparation device comprises means for opening the reservoir so that the first and the second medium are mixed with each other. Accordingly, the fluid preparation device, i.e., a part thereof comprises a means for opening the reservoir so that it is not necessary for the personnel to take any steps regarding this opening action for preparing the concentrate or the solution.

The reservoir may be a part of the container or may be formed by a separate part.

If for example said means for opening the reservoir are mounted to a lid which is moved by a user after inserting the container into the mounting connector part opening of the reservoir is ensured automatically without any further interaction by the user.

Accordingly, the opening of the reservoir does not require any particular attention by the user.

According to a preferred embodiment of the invention, the fluid preparation device comprises a mounting connector part suitable for mounting and connecting the connecting portion of the container wherein the mounting connector part at least in part comprises said line, such as the flushing fluid line and the prepared fluid line. According to the invention the flushing line and the prepared fluid line may be formed by one and the same line or by different lines.

In accordance with a preferred embodiment the mounting connector part comprises at least one mounting means, such as first and second mounting means which are adapted to mate with at least one mounting means, such as first and second mounting means of the connecting portion of the container so that the one or more mounting means of the mounting connector part are in fluid communication with the one or more mounting means of the connecting portion of the container.

As outlined above in accordance with a further preferred embodiment of the invention the fluid preparation device comprises a lid, wherein the lid comprises the means for opening the reservoir. By moving the lid either automatically or by action of the user the means for opening the reservoir are moved simultaneously so that the reservoir is opened automatically and no further interaction by the user is required.

The lid may be turnable around a joint, preferably from a first to a second position, wherein in the first position of the lid the reservoir is still closed and in the second position of the lid the reservoir is opened by said means for opening the reservoir.

Furthermore, the fluid preparation device may comprise at least one mechanical stop which is adapted to restrict the scope of movement of the means for opening the reservoir. This mechanical stop may be adapted to restrict the movement of the means for opening the reservoir, for example by abutment. The mechanical stop preferably forms one or more abutments which adjust the position of the means for opening the reservoir so that these means are moved in the correct direction and into the correct position with regard to the reservoir and in particular with this part of the reservoir which has to be opened by the means for opening the reservoir.

For example, the means for opening the reservoir may be moveable around a joint or axis and this scope of movement can be restricted by one or more mechanical stops.

Furthermore the fluid preparation device may comprise at least one spring which interacts with the means for opening the reservoir. This spring may be adapted to adjust the position of the means for opening the reservoir in the desired fashion.

Furthermore, the reservoir may contain a housing, preferably a cylindrical housing, as well as a piston which is moveable relative to the housing in a first direction. In a further preferred embodiment the means for opening the reservoir interacts with the piston in said first direction or basically in said first direction. This embodiment improves opening of the reservoir and avoids any delay or other difficulties in opening the reservoirs caused for example by tilting the piston relative to the housing.

In accordance with a further preferred embodiment of the invention one or more sensors are provided for sensing the position of the means for opening the reservoir and/or for sensing the position of the support to which the means for opening the reservoir are mounted, such as the lid. For example, those sensors may be formed by Hall sensors.

Furthermore, one or more fixing means may be provided for fixing the means for opening the reservoir or for fixing the support to which the means for opening the reservoir are mounted in a certain predefined position.

The sensing means may be used to give a feedback to the fluid preparation device or to the user that opening of the reservoir took place and that the means for opening the reservoir are in a correct position.

The present invention further relates to a fluid preparation device, such as a dialysis machine, which is suitable for mounting and connecting the connecting portion of a container, wherein the fluid preparation device comprises at least one line, such as a flushing line and a prepared fluid line and wherein the fluid preparation device is adapted such that the at least one line can be brought in fluid communication with the interior of the container at least in the connected position of the container.

According to the invention the container is filled with a first medium. This fluid preparation device is characterized in that the reservoir contains a second medium, wherein the fluid preparation device comprises means for opening said reservoir.

Preferably, the first medium and the second medium are solids, such as a powder. However, the present invention is not limited to this embodiment. Accordingly the first medium and/or the second medium may be present in liquid form.

The fluid preparation device may comprise a lid, wherein the lid comprises the means for opening the reservoir. Preferably the lid is turnable around a joint, preferably from a first position to a second position, wherein in the first position the reservoir is still closed and in the second position the reservoir is opened.

Basically the first medium which is located in the container may be a solid, such as a powder containing electrolytes, such as $NaCl_2$, $KCl$, $MaCl_2$, $CaCl_2$ as well as preferably glucose or any other osmotic agent. Preferably the first medium comprises all constituents for preparing an acidic concentrate, except the acid. Preferably the acid, i.e. the second medium is present in the reservoir.

Preferably after mixing the first and the second medium water is supplied into the container in order to form a concentrate, preferably an acidic concentrate which is used (together with a basic concentrate) for the preparation of a final dialysis solution.

The second medium is mixed with the ingredients of the container after opening the reservoir.

The present invention further relates to a method for the preparation of a composition, in particular for a composition for preparing an acidic concentrate for a dialysis fluid, by use of a combination as described herein, wherein the method of comprises the following steps:
   a) putting the container with its connection portion into the fluid preparation device,
   b) moving the means for opening the reservoir of the container, and
   c) opening the reservoir affected by said movement of the means for opening the reservoir and mixing the first medium and the second medium.

As outlined above it is preferred that the lid comprises the means for opening the reservoir and moving the means for opening the reservoir is performed by moving the lid.

The composition in the container after opening the reservoir is preferably a solid.

Preferably the lid is pivoted around an axis.

According to a further preferred embodiment of the invention the direction of the movement of the means for opening the reservoir at least in part and preferably after contacting the reservoir corresponds or basically corresponds to the direction in which a piston of the reservoir is moveable relative to the housing of the reservoir.

BRIEF DESCRIPTION OF THE DRAWINGS

The invention is described below in more detail using embodiments shown in the following figures as follows.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
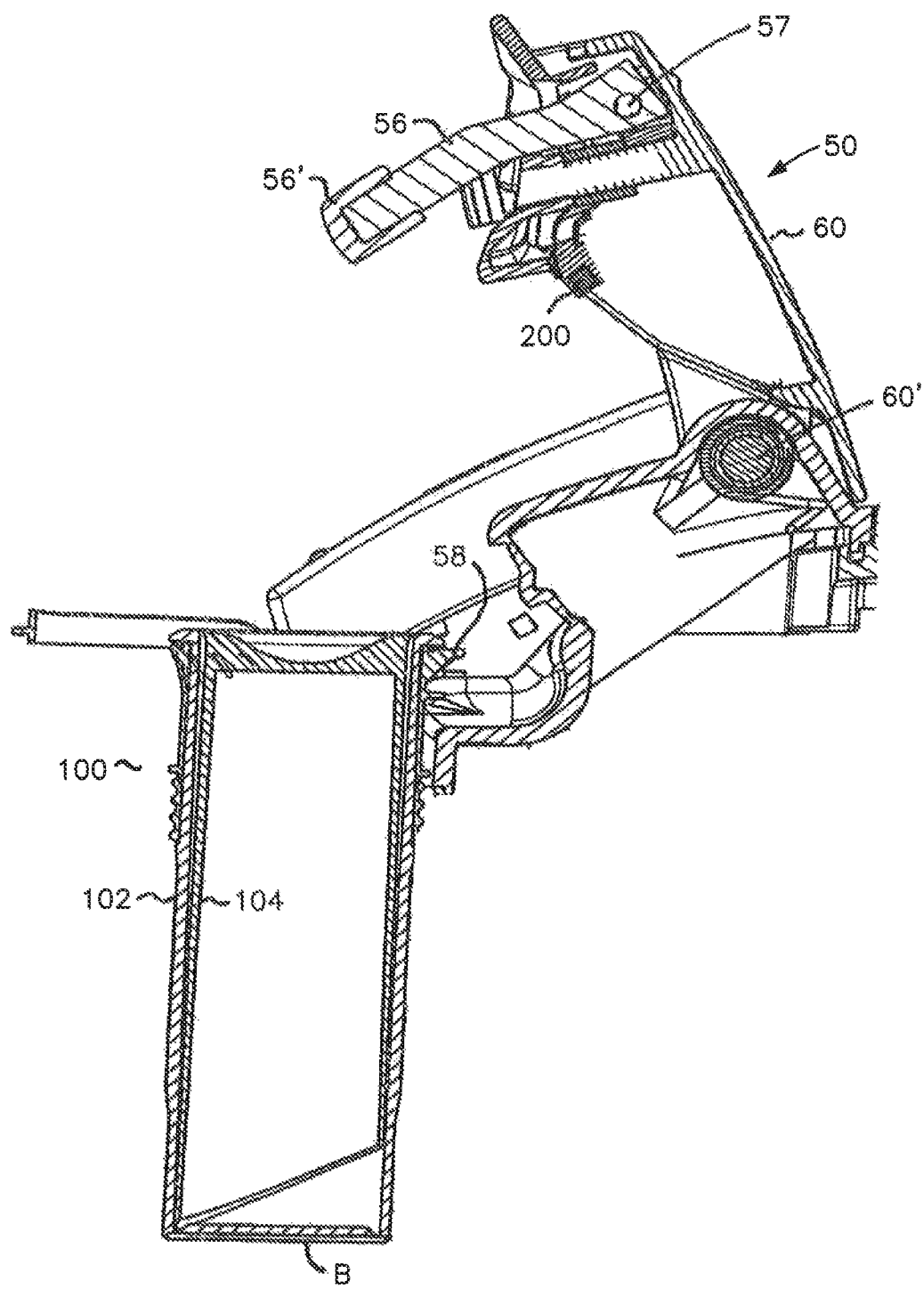
FIGS. 1-3: sectional views of the reservoir and of the mounting connector part as well as of the lid in different positions of the lid.

FIG. 1 shows the lid 60 in a first, opened position. In this position, the means for opening the reservoir 56 which consists of a rod, made for example of metal, and a cover 56' which is made for example from plastics, is not in contact with the reservoir.

As shown in FIG. 1 one end of the rod 56 is provided with said cover 56'. The other end of the rod 56 is pivotally connected via a joint or axis 57 to the lid 60.

Accordingly, the rod 56 is not fixedly mounted to the lid 60 but is moveable within a predefined range.

Figure 7:
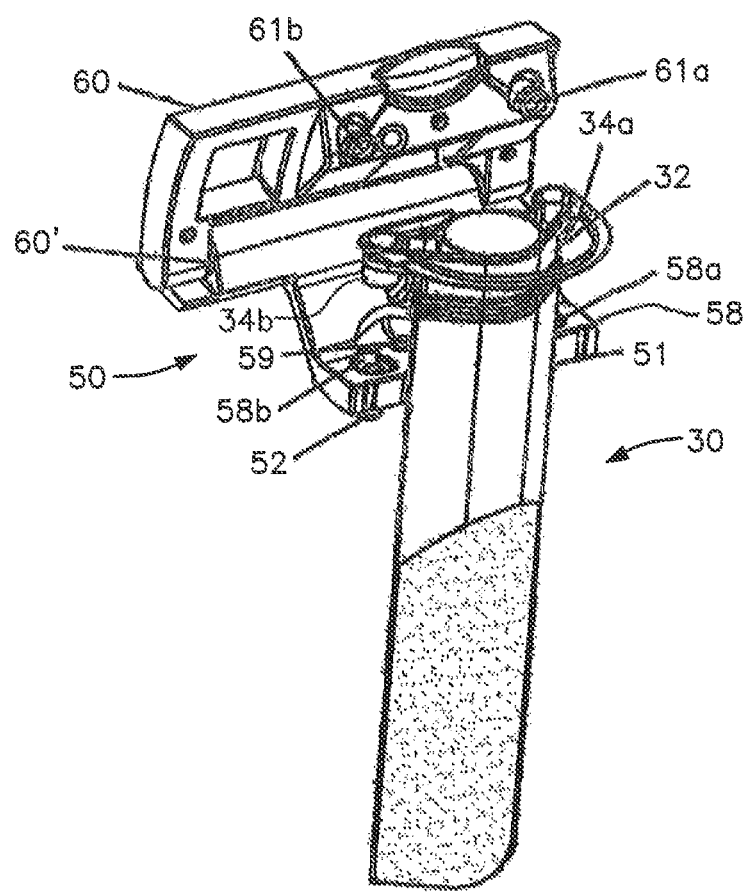
FIG. 7: a perspective view of the container, the mounting connector part and the lid
Figure 8:
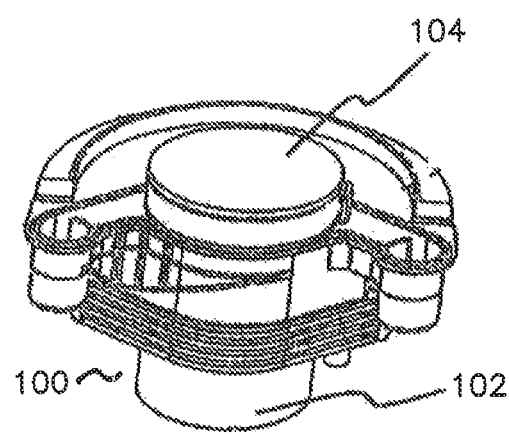
FIG. 8: a perspective view of the connecting portion of the container together with the reservoir.

As further shown in FIG. 1 the fluid preparation device 50 not only comprises the lid 60 but also a mounting connector part 58 which is adapted to be connected to a container. Reference is made to FIG. 7 and the corresponding explanations above which are part of this invention as well.

The container which is not shown in FIGS. 1-6 is connected with or arranged below the reservoir 100 which comprises a housing 102 as well as a piston 104 which is moveable relative to the housing 102. The reservoir is filled with a second medium which is different to the medium contained in the container.

In accordance with a preferred embodiment the reservoir 100 is filled with a liquid such as an acid.

As shown in FIG. 1 the piston 104 has a slanted lower edge, which provides as a cutting tool for opening the button B of the housing 102 of the reservoir 100.

Figure 2:
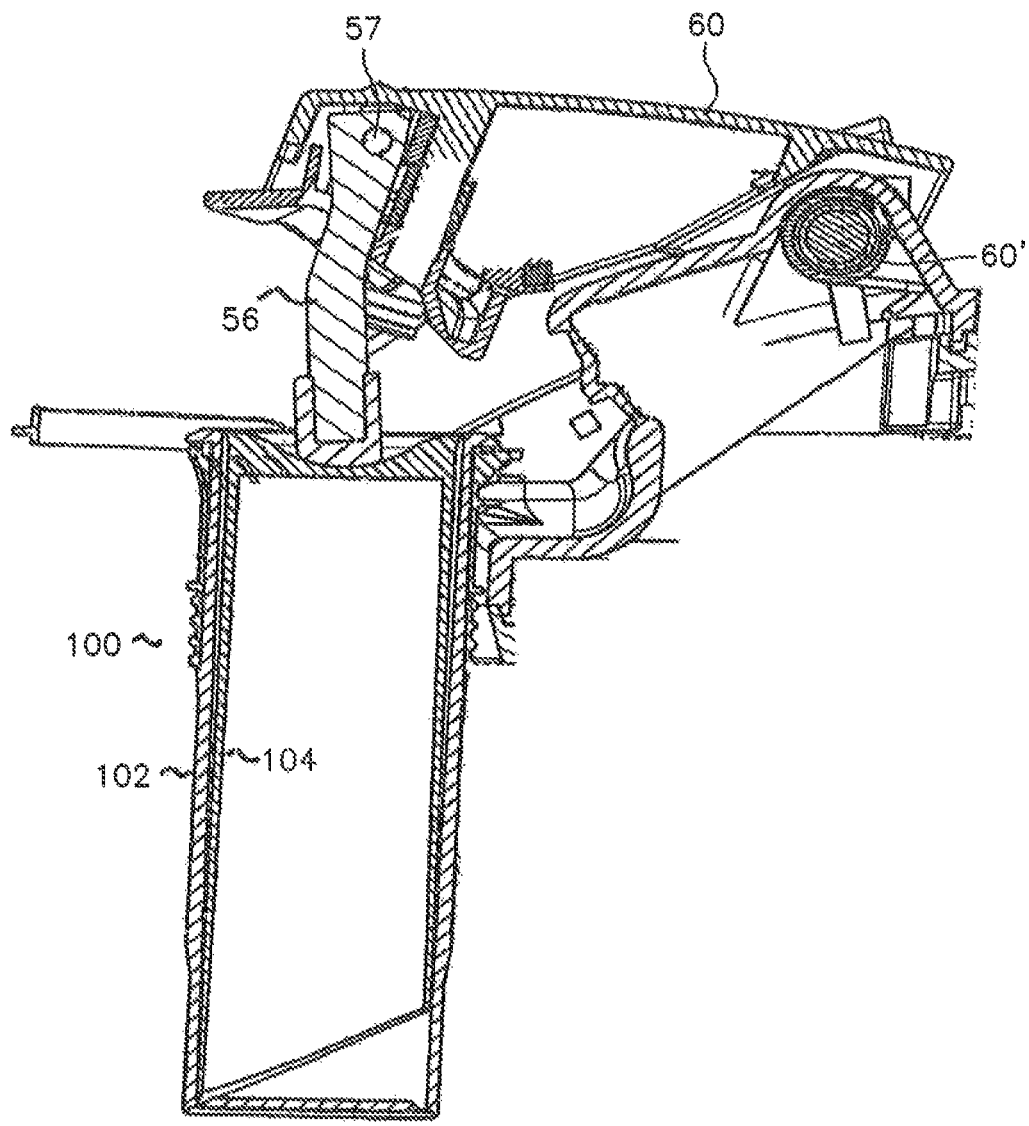

The movement of the lid 60 from the position shown in FIG. 1 around axis 60' to the position shown in FIG. 2 results in a contact between the rod 56 or the cover 56' with the upper portion of the piston 104 which has an indentation as shown in the figure. This situation is shown in FIG. 2. In this position of the lid 60 the reservoir 100 is still closed so that its content is not mixed with the content of the container. The rod 56 is accommodated in said indentation.

Figure 3:
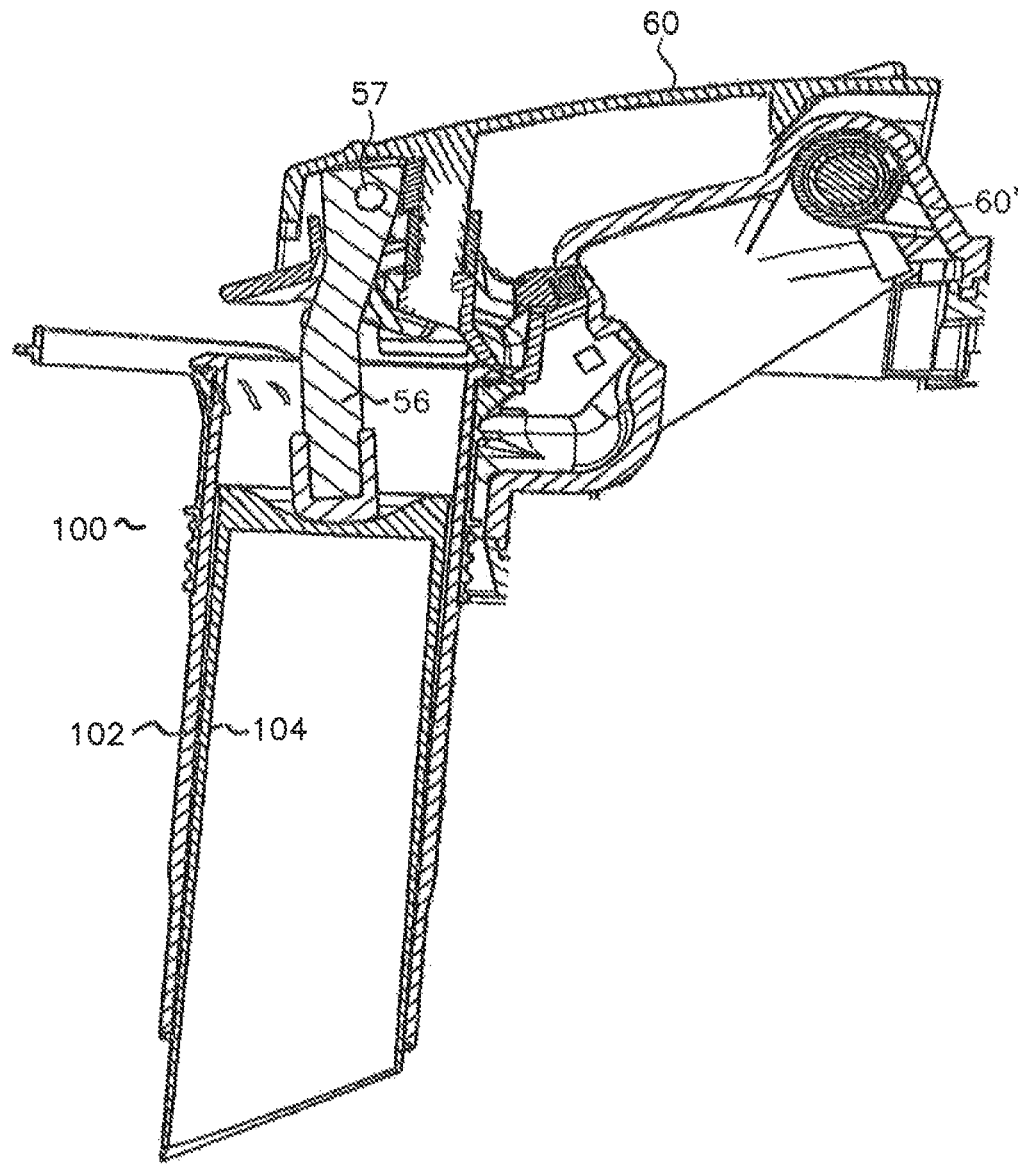

If the lid 60 is pressed downwards starting from FIG. 2 to the position shown in FIG. 3, the rod 56 moves the piston 104 in a downward direction relative to the housing 102, and the lower slanted edge of the piston 104 opens the button B of the reservoir 100 so that the second medium such as an acid is emptied from the reservoir into the container. The aforementioned position is shown in FIG. 3.

As outlined above the container may comprise electrolytes, preferably in a solid form. In addition the container may comprise preferably solid osmotic agents such as glucose.

The reservoir 100 preferably contains an acid, preferably a solid acid, which is mixed with the content of the container upon opening of the reservoir.

As shown in FIG. 3 the downward movement of the lid inevitably results in an opening of the reservoir so that the likelihood that the reservoir is closed although the lid is in its closed downward position is minimized.

Figure 4:
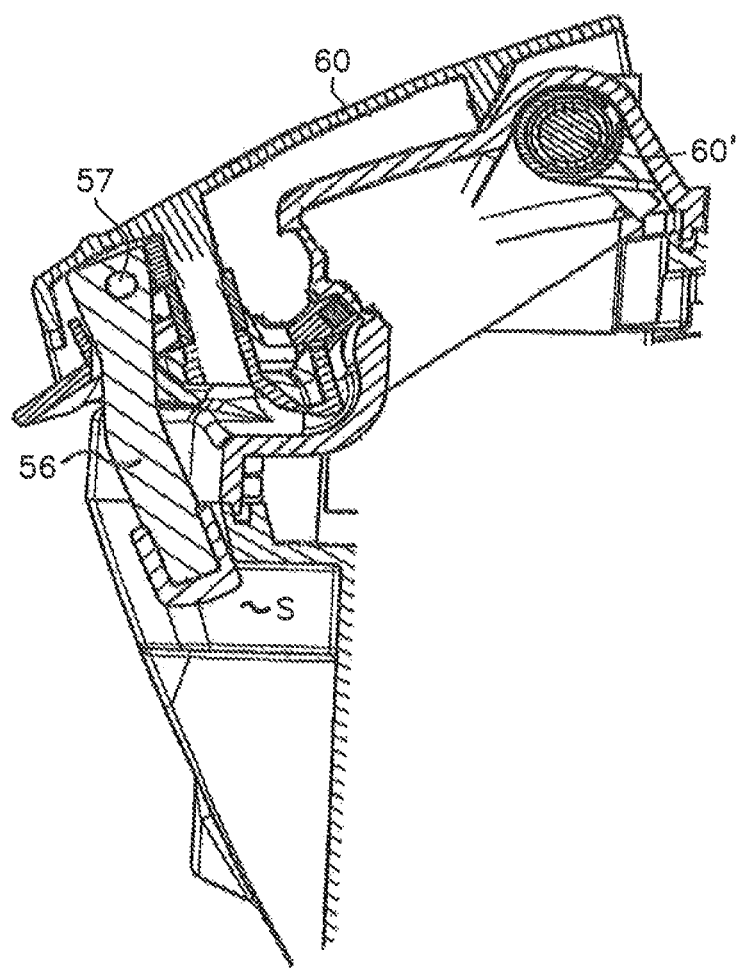
FIG. 4: a further cross-sectional view of the mounting connector part and of the lid in a closed position without reservoir.

FIG. 4 shows a position in which no container is located in the mounting connector part of the fluid preparation device. In this case, the lid is completely closed and the rod may be accommodated in a space of the mounting connector part which is designated with reference character S.

Figure 5:
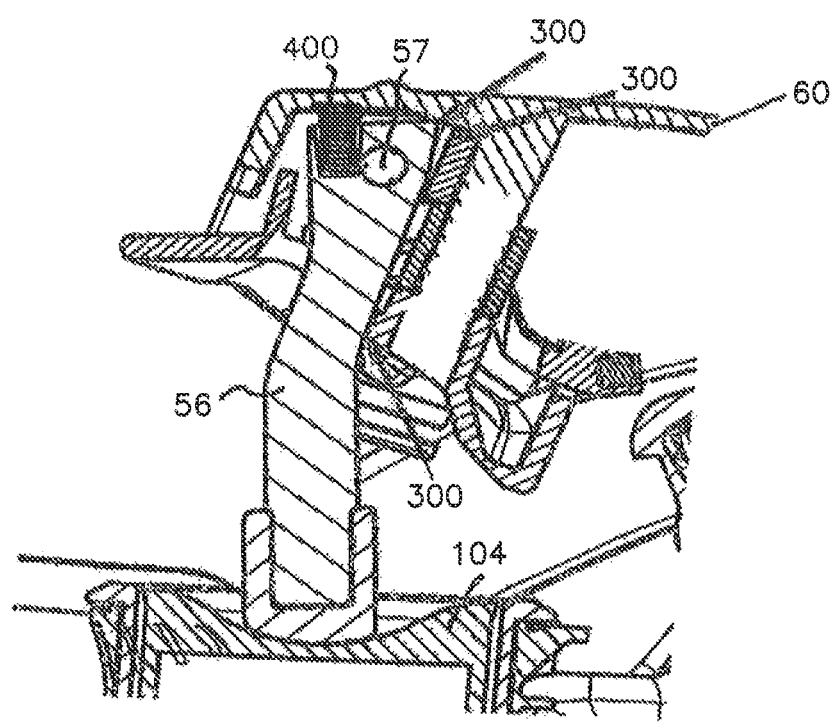
FIG. 5: a further cross-sectional view of the lid and of the means for opening the reservoir.

As outlined above and as shown in more detail in FIG. 5 the rod 56 is not fixedly mounted at the lid but is moveably relative to the lid, e. g. via axis 57. The arrows in FIG. 5 designate mechanical stops 300 which are formed by abutments which limit the pivoting movement of the rod 56 relative to the axis 57.

Furthermore, reference numeral 400 designates a spring which interacts with the rod so that a force is posed into the rod preferably in the direction of the mechanical stops.

If the lid 60 is moved from the position shown in FIG. 1 to the position shown in FIG. 3 the lid performs a rotational movement around axis 60'. In case that the rod 56 would be fixedly mounted to the lid 60 the rod 56 would exactly make the same kind of movement as the lid 60. This might have the effect that the rod 56 would be moved in a lateral direction after contacting the piston in FIG. 2 which might lead to a tilting or any other dysfunction of the opening of the reservoir.

Due to the flexible mounting of the rod 56, i.e., by any means of a joint, hinge, axis, etc., a smooth and steady movement of the piston is realized.

Figure 6:
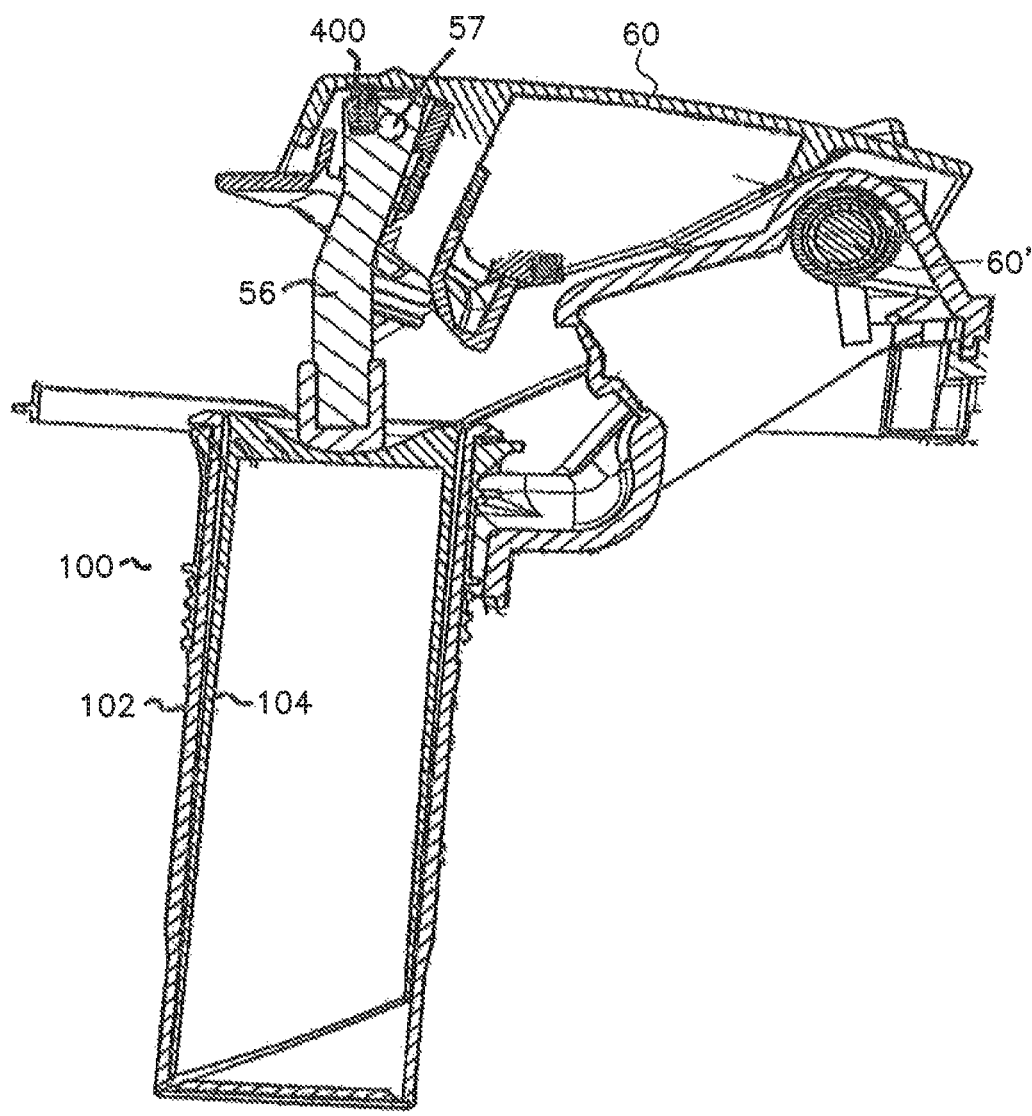
FIG. 6: a further cross-sectional view of the embodiment according to FIG. 5 together with the mounting connector part and the reservoir.

FIG. 6 shows the embodiment of FIG. 5 together with the reservoir 100 in the position of the rod 56 which corresponds to the position shown in FIG. 2.

The use of at least one spring and at least one mechanical stop ensures that the rod is positioned on the piston in the correct position and orientation.

As further outlined above one or more sensors 200, such as Hall sensors, may be provided for detecting the position of the lid and/or of the means for opening the reservoir, such as the rod. These sensors may be connected with a controller which is adapted so as to allow the start of the treatment depending on the signal of the sensor. If the sensor detects a position of the lid and/or of the means for opening the reservoir which is not the correct one, this controller may inhibit the start of the treatment because it is assumed that the reservoir has not been opened.

Furthermore, the connecting portion of the container or any other part of the container such as a reservoir may have identification means for identification of the container and in particular of the content thereof. Reading means may be provided which read out those identification means and allow start of the treatment only if the correct identification has been verified.

Furthermore there may be provided fixing means for fixing the lid in one or more predetermined positions to secure the correct operation of the device.

Furthermore there may be one or more channels for ventilating the interior of the container when the fluid is drained from the container. Those channels may be provided in the mounting connector part and/or in the connecting portion of the container.

Referring to the embodiment of FIG. 7, the fresh fluid may be guided into the container by line 52, the mounting means 34b and 58b and preferably by means of a tube within the container according the embodiment shown in DE 10 2011 106 248 A1 and the prepared solution may be drained from the container by the same line.

Alternatively the fresh fluid line and the prepared fluid line may be different parts of the arrangement. Accordingly the fresh fluid line may be line 51 and the prepared fluid line may be line 51 as explained above with respect to the embodiment disclosed in EP 1 344 550 B1.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A combination comprising:
   a container having a connecting portion; and
   a fluid preparation device configured for mounting and connecting the connecting portion of the container,
   the fluid preparation device including at least one line in fluid communication with an interior of the container in a connected position of the container,
   the container being filled with a first medium, and
   including a reservoir containing a second medium, with the reservoir including a housing, and a piston which is movable relative to the housing in a first direction,
   the fluid preparation device including an element for opening the reservoir so that the first medium and the second medium are mixed with each other, and a lid, with the lid including the element for opening the reservoir, and
   with the element for opening the reservoir being rod-shaped and pivotably fixed to the lid, to interact with the piston is essentially the first direction, so as to open the reservoir.

2. The combination according to claim 1, wherein the at least one line includes a flushing fluid line for feeding a fluid into the interior of the container, and a prepared fluid line for guiding a prepared fluid out of the interior of the container, and wherein the flushing fluid line and the prepared fluid line are formed by a same line or by different lines.

3. The combination of claim 1, wherein the fluid preparation device includes a mounting connector part configured for mounting and connecting the connecting portion of the container, wherein the mounting connector part at least in part includes the at least one line, and wherein the mounting connector part includes at least one mounting element configured to mate with at least one mounting element of the connecting portion of the container, so that the mounting element of the mounting connector part is in fluid communication with the mounting element of the connecting portion of the container.

4. The combination of claim 1, wherein the lid is turnable around a joint or axis from a first position to a second position, and wherein in the first position of the lid the reservoir is still closed and in the second position of the lid the reservoir is opened.

5. The combination of claim 1, wherein the fluid preparation device includes at least one mechanical stop adapted to restrict a range of movement of the element for opening the reservoir.

6. The combination of claim 1, wherein the fluid preparation device includes at least one spring which interacts with the element for opening the reservoir.

7. The combination of claim 1, further comprising at least one of
   one or more sensors for sensing a position of the element for opening the reservoir or for sensing a position of a support to which the element for opening the reservoir is mounted, and
   one or more fixing elements for fixing the element for opening the reservoir or for fixing the support to which the element for opening the reservoir is mounted.

8. The combination according to claim 1, wherein the fluid preparation device is a dialysis machine.

9. The combination according to claim 1, wherein the housing is cylindrical.

10. A method of preparing a composition for preparing a dialysis fluid, the method comprising the following steps:
    a) with a container having a connecting portion, and a fluid preparation device configured for mounting and connecting the connecting portion of the container, the fluid preparation device including at least one line in fluid communication with an interior of the container in a connected position of the container, the container being filled with a first medium, and including a reservoir containing a second medium, with the reservoir including a housing, and a piston which is movable relative to the housing in a first direction, the fluid preparation device having an element for opening the reservoir so that the first medium and the second medium are mixed with each other, and a pivotable lid, with the lid including the element for opening the reservoir, and with the element for opening the reservoir being rod-shaped and pivotably fixed to the lid,
    putting the container with the connection portion thereof into the fluid preparation device;
    b) pivotably moving the lid such that the element for opening the reservoir movably actuates the piston in essentially the first direction; and
    c) by the actuating of the piston, opening the reservoir so as to mix the first medium and the second medium.

* * * * *